United States Patent [19]

Suzuki

[11] 4,016,208

[45] * Apr. 5, 1977

[54] ACID PRODUCTION

[75] Inventor: Shigeto Suzuki, San Francisco, Calif.

[73] Assignee: Chevron Research Company, San Francisco, Calif.

[*] Notice: The portion of the term of this patent subsequent to Oct. 7, 1992, has been disclaimed.

[22] Filed: Apr. 29, 1975

[21] Appl. No.: 572,780

Related U.S. Application Data

[63] Continuation-in-part of Ser. No. 480,894, June 19, 1974, Pat. No. 3,911,003.

[52] U.S. Cl. .................... 260/535 R; 260/535 P
[51] Int. Cl.² .................................. C07C 59/06
[58] Field of Search ...................... 260/535 R

[56] References Cited

UNITED STATES PATENTS 3,673,156  6/1972  Cevidalli .................. 260/535 R

Primary Examiner—Paul J. Killos
Attorney, Agent, or Firm—J. A. Buchanan, Jr.; John Stoner, Jr.; W. Keith Turner

[57] ABSTRACT

A process for producing hydroxyacetic acid which comprises contacting carbon monoxide with formaldehyde and a catalyst comprising hydrogen fluoride in a reaction zone at a temperature between 0° and 100° C and a pressure between 10 and 4000 psig. Oxydiacetic acid is also produced by this reaction. The ratio of hydroxyacetic acid to oxydiacetic acid is increased by adding water to the reaction mixture.

7 Claims, 1 Drawing Figure

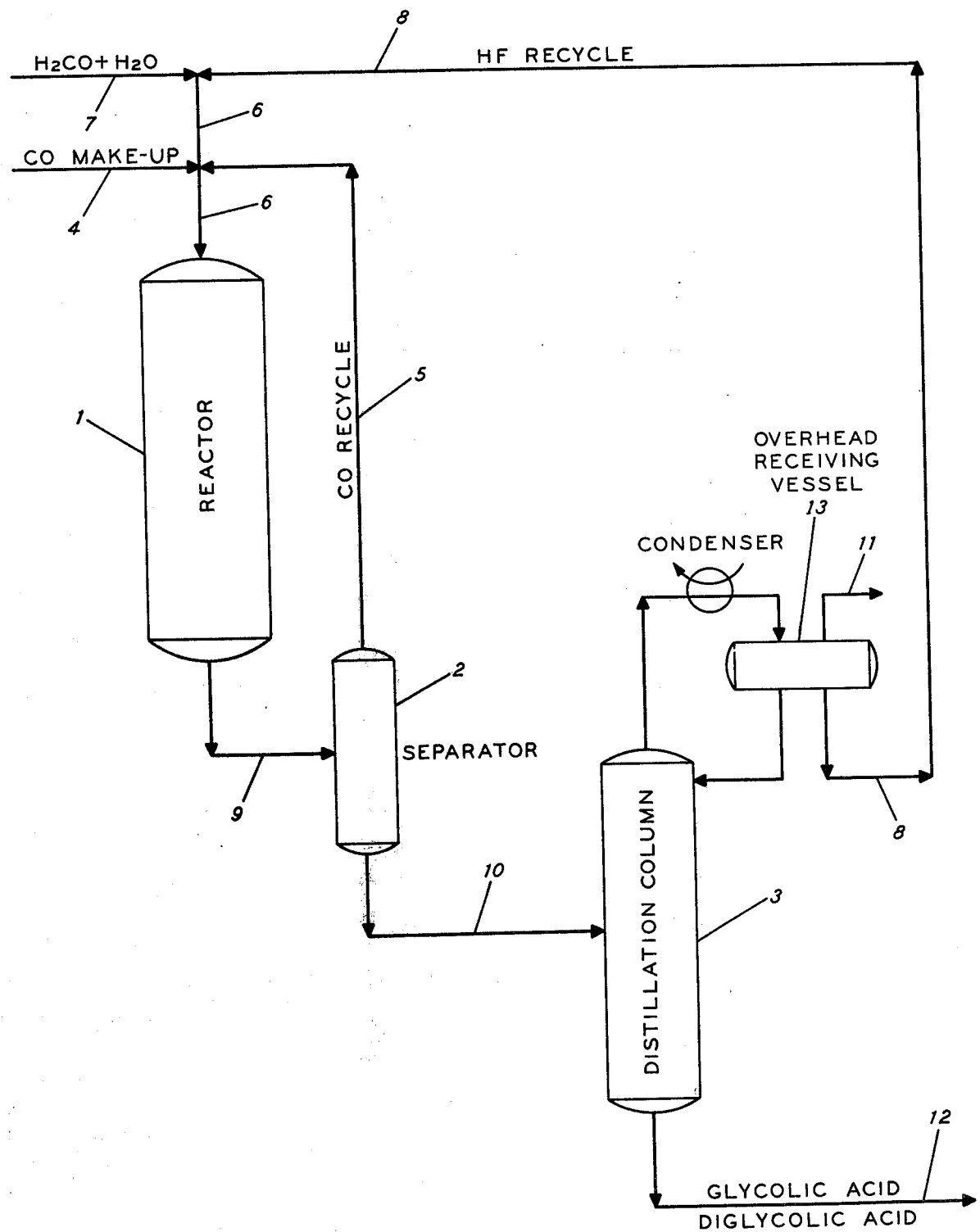

ACID PRODUCTION

CROSS-REFERENCE TO RELATED APPLICATION

This application is a continuation-in-part of U.S. application Ser. No. 480,894, filed June 19, 1974, now U.S. Pat. No. 3,911,003 the disclosure of which is incorporated herein by reference.

BACKGROUND OF THE INVENTION

The present invention relates to reaction of carbon monoxide with formaldehyde, preferably in the presence of water, to obtain hydroxyacetic acid.

Hydroxyacetic acid has various known uses and can be used to make ethylene glycol. In the reaction steps important to the current commercial production of hydroxyacetic acid, formaldehyde is reacted with carbon monoxide and water in the presence of an acidic catalyst such as sulfuric acid at a high pressure, above 4500 psi, and at a temperature usually between about 150° and 225° C.

U.S. Pat. Nos. 2,152,852; 2,153,064; and 2,265,945 disclose hydroxyacetic acid production from formaldehyde, carbon monoxide and water using acid catalysts. According to all three of these patents, the acid catalysts disclosed are hydrochloric, sulfuric, phosphoric and inorganic acid salts such as potassium acid sulfate, sodium acid phosphate and boron fluoride. Temperatures disclosed for use in the processes of the patents are 50° to 350° C and more preferably 140° to 225° C. Pressures disclosed are 5 to 1500 atmospheres (75 to 23,000 psi) and higher. In the examples of all three of the patents, the only inorganic acid catalysts used are phosphoric acid, sulfuric acid and hydrochloric acid. The temperatures used in the examples of the patents usually are between 160° and 200° C; and the pressures usually about 900 (13,500 psi) atmospheres and essentially always above 300 atmospheres (4500 psi). The severe reaction conditions indicated for the carbonylation of formaldehyde such as the high reaction temperature in the presence of corrosive acids and very high CO pressure require expensive equipment made from corrosive-resistant materials. According to the disclosure in the patents, the reaction can be effected in a continuous manner by passing the formaldehyde or its equivalent, water or its equivalent, and acid catalyst through a reaction zone either cocurrently or countercurrently to the flow of carbon monoxide.

SUMMARY OF THE INVENTION

According to the present invention, a process is provided for producing hydroxy-acetic acid, which process comprises contacting carbon monoxide with formaldehyde, water and a catalyst comprising hydrogen fluoride in a reaction zone and under reaction conditions effective to form hydroxyacetic acid, including a temperature between 0° and 100° C, preferably 0° to 60° C, and a carbon monoxide partial pressure between 10 and 4000 psig.

Preferably the reaction is carried out in the presence of water, for example up to about 25 weight percent of water based on the total weight of formaldehyde, hydrogen fluoride and water. I have found that the presence of water increases the amount of hydroxyacetic acid produced in the process of the present invention. I have found that oxydiacetic acid can be, and typically is, produced by the process of the present invention. When the reaction is carried out under anhydrous conditions, oxydiacetic acid is obtained in predominant yeilds compared to the yield of hydroxyacetic acid.

According to a preferred embodiment of the present invention, the temperature used in the reaction zone is between 20° and 60° C and the pressure between 10 and 4000 psig, more preferably 10 to 3000 psig. Unless otherwise stated, pressures given herein refer to carbon monoxide partial pressure. However, typically the total pressure is not much above the carbon monoxide partial pressure, carbon monoxide being by far the most volatile of the reactants and products. Usually the total pressure is only 1 to 10% higher than the carbon monoxide partial pressure.

Among other factors, the present invention is based on my finding that in the presence of an HF catalyst high yields of hydroxyacetic acid are obtained from the carbon monoxide, formaldehyde and water reactants even at moderate temperatures and pressures and within a commercially reasonable reaction time.

Other constituents may be present with the HF catalyst, although in any case HF is a critical component of the catalyst and must be present. Suitable added constituents are metal salts, e.g., cuprous or cupric oxide, silver oxide, nickel oxide, chromium oxide; halogen acids, e.g., HBr, HCl, HI. The metal salts probably are converted to the fluorides in the reaction zone.

I have found that a particularly preferred added constituent is $HBF_4$, which may be added, for example, as $BF_3$. The presence of $HBF_4$ was found to increase the rate of reaction and thus can be used to improve yield or reduce the reactor size. These benefits must be weighted against the increased difficulty (compared to use of HF free of $HBF_4$) in removing the by-product compounds in order to purify the organic acid product.

In the presence of the HF catalyst, the reaction to produce hydroxyacetic acid is suprisingly rapid. The rate of reaction is so high that even at moderate temperatures in the range of 20° and 60° C the reaction can be completed in relatively short reaction times. Whereas, at those temperatures, i.e., 20° to 60° C, and in the presence of other acidic catalysts, e.g., sulfuric acid, the reaction is so slow as to be essentially stopped. Moderate temperatures are desirable because reactor corrosion is less at lower temperatures. With an HF catalyst, stainless steel reactors are possible, whereas at the high temperatures required for other acids, the reactor should be made of more expensive materials, e.g., Hastelloy alloy, titanium, etc.

In addition to the relatively lower temperature and pressure used in the present invention compared to prior art processes using hydrochloric or sulfuric acid catalysts, the HF catalyst used in the present invention is relatively easy to handle and to separate from the reaction zone effluent of the present invention. Since the boiling point of HF is 19.7° C at one atmosphere pressure, which is considerably more volatile than water, and hydroxyacetic acid is not distillable under reasonable temperature and pressure, the HF catalyst can be readily separated by distillation and recycled to the reaction zone. Some unreacted formaldehyde may also be codistilled with HF and be recycled to the reaction zone. Since sulfuric acid has a high boiling point of 230° C even at a reduced pressure of 40 mm Hg also is an oxidizing agent for organic compounds at an elevated temperature, its separation from the non-volatile hydroxyacetic acid product cannot conveniently be done using a simple distillation, but must rely on other more expensive separation techniques such as fractional crystallization of hydroxy-acetic acid or precipitating sulfuric acid as its insoluble salts.

Hydrochloric acid, on the other hand, has a very low boiling point of −84° C at one atmosphere pressure, and is gaseous at room temperature with the vapor pressure of about 700 psi, which will cause a considerable added reaction pressure in the carbonylation of formaldehyde at a higher reaction temperature. Also, the separation of hydrochloric acid from a reaction product and recycling to the reaction zone will be more costly due to its low boiling point and high vapor pressure.

Boron trifluoride readily reacts with water and alcohols to form higher boiling boric acid and it derivatives, and thus, its simple separation from the hydroxyacetic acid product and recycle is rather difficult. In this respect see, e.g., R. I. Durant and B. Durant, "Introduction to Advanced Inorganic Chemistry," John Wiley and Sons, Inc., New York, N. Y., 1962, p. 501.

Preferably, the carbon monoxide pressure in the reaction zone is kept at 10 to 4000 psig and formaldehyde, water and HF are fed to the reaction zone at a mol percent of 3 to 35% formaldehyde, 3 to 40% water; and 40 to 90% HF. Paticularly preferred feed compositions are 10 to 3000 psig carbon monoxide pressure; and mol percent of 5 to 25 formaldehyde; 5 to 30 water; and 50 to 85 HF.

The ratio of condensed reactants and catalyst may also be expressed on a weight basis, e.g., approximately as follows: formaldehyde, 5 to 50%; water , 2 to 25%; and HF, 40 to 93%. More preferable ranges are: formaldehyde, 5 to 30%; water, 4 to 20%; and HF, 45 to 85%. Within these ranges it is particularly preferred to maintain a formaldehyde:water weight ratio below about 4:1 for maximum glycolic acid (hydroxyacetic acid) production. At higher ratios I have found that increasing amounts of diglycolic acid are produced. Under anhydrous conditions and at high concentrations of formaldehyde in HF, diglycolic acid (oxydiacetic acid) is the predominant product.

If the process of the present invention is carried out batchwise rather than continuous, suitable carbon monoxide pressure and weight or mol fractions for the reactants and HF catalyst in the reaction zone are in the ranges as given above for a continuous process.

The carbon monoxide used in the process of the present invention can be passed either cocurrently or counter-currently to the formaldehyde and water reactants. In accordance with a preferred embodiment, a synthesis gas stream comprirsing hydrogen and carbon monoxide is passed counter-current to formaldehyde, water and the HF catalyst in cascade fashion so that the carbon monoxide is reacted out of the upward-flowing synthesis gas stream and a purified gas stream of reduced carbon monoxide content is obtained. The resulting hydrogen-rich gas stream can be used in various hydrogenation processes.

The oxydiacetic acid or diglycolic acid produced by the process of the present invention can be depicted as follows:

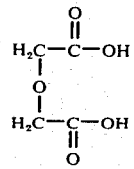

THE DRAWING

In the embodiment of the process as shown in the drawing, reactants are combined and pass downwardly through a reactor. Excess feedstocks are recycled. The drawing is a simplified schematic process flow diagram illustrating one continuous process embodiment of the present invention to produce glycolic acid from the HF-catalyzed reaction of formaldehyde, carbon monoxide and water.

Exemplary data for the drawing as follows were calculated based on experimental data. Referring to the drawing, make-up carbon monoxide is introduced via line 4 at 11,690 parts per hour by weight and is combined with 11,680 parts per hour recycle carbon monoxide introduced via line 5, and charged to reactor 1 via line 6. The recycle carbon monoxide stream also contains 120 parts per hour of formaldehyde and 20 parts per hour of hydrogen fluoride. At the same time, 77 weight percent aqueous formaldehyde, 16,260 parts per hour in line 7, and hydrogen fluoride, 20,850 parts per hour in line 8, are charged to the reactor via line 6. The reactor is maintained at 49° C and 1500 psig. The product stream, 60,620 parts per hour, is removed through line 9, and charged to a separator vessel 2 maintained at 49° C and about 1490 psig. Here unreacted carbon monoxide and formaldehyde are vaporized and sent back to the reactor via line 8. The product stream from the separator is next passed to stripper column 3 via line 10. In the stripper column 20,850 parts per hour HF is distilled overhead at 17 psig and 43° C and is recycled to the reactor through line 8. A small amount of carbon monoxide, 10 parts per hour, is lost from the reflux drum 13 through line 11. The bottoms are removed from the stripper via line 12 at 27,940 parts per hour. These bottoms consist of a 95/5 weight percent mixture of glycolic acid and diglycolic acid values. That is, the product is a mixture of glycolic acid, diglycolic acid, and compounds such as glycolyl glycolate, etc., which are readily hydrolyzed to glycolic acid or diglycolic acid.

Purification may be accomplished in several ways. In cases where the glycolic acid is intended as a feedstock in ethylene glycol production, the entire bottoms product may be esterified with methanol and then catalytically hydrogenated. The resulting mixture of ethylene glycol and diethylene glycol is readily separated by distillation.

The methyl esters may also be separated by distillation and each fraction hydrolyzed to glycolic acid and diglycolic acid respectively. Both acids are items of commerce.

EXAMPLES

Example 1

A 300-ml magnetically stirred autoclave made of stainless steel was charged with 0.30 mol formaldehyde, 0.55 mol water, and 5 mol hydrogen fluoride.

The autoclave was pressurized with carbon monoxide to 2025 psig at −1° C and sealed, and stirring was started. The CO pressure dropped to 1520 Zpsig within 10 minutes while the temperature rose to 22° C, and the CO uptake stopped at this point. The CO reacted was one molar equivalent to formaldehyde charged. Hydrogen fluoride was distilled out of the reaction mixture and the distillation bottoms essentially consisted of glycolic acid. Bottoms analysis was made by thermally methylating an aliquot with excess methanol and subjecting the resulting ester to gas chromatography. Formaldehyde conversion was essentially complete and a 95 mol percent yield of glycolic acid was obtained.

EXAMPLE 2

An autoclave was charged with 0.3 mol formaldehyde, 0.42 mol water and 3.7 mols hydrogen fluoride. The autoclave was pressured with CO to 1000 psig and sealed at 2° C. One equivalent of CO to formaldehyde was taken up in about ten minutes while the temperature rose to 24° C. The final CO pressure was 655 psig. The analysis of the product indicated 97 mol percent yield of glycolic acid with complete conversion of formaldehyde.

EXAMPLE 3

In a manner similar to Example 1, 0.15 mol formaldehyde, 0.28 mol water and 2.5 mols HF were reacted with CO. The initial and final CO pressures were respectively 500 and 355 psig and initial and final temperatures 0° and 22° C. One equivalent of CO to $H_2CO$ was taken up in 24 minutes. The analysis showed almost complete and quantitative conversion of formaldehyde to glycolic acid.

EXAMPLE 4

The process of Example 1 was carried out, except that the autoclave was charged with 0.5 mol of formaldehyde, 0.5 mol of water and 2.5 mol of hydrogen fluoride at a temperature of −40° C. Initial carbon monoxide pressure was 2000 psig. After 30 minutes of reaction time, during which the temperature rose to 37° C. and the pressure dropped to 1600 psig, the reaction mixture was removed and analyzed. The formaldehyde conversion was over 99 mol percent, and the yield of glycolic acid was essentially quantitative.

EXAMPLE 5

In this example a reactor was charged with 25.1 g (0.7 mol) of formaldehyde, 15.1 g (0.7 mol) of water and 59.8 g (2.5 mols) of hydrogen fluoride. The reactor was then pressured to 1000 psig with carbon monoxide at 50° C. Each time that the pressure dropped to 500 psig, the reactor was recharged to 1000 psig with carbon monoxide. After 60 minutes of reaction time, the conversion of formaldehyde was complete, and the yield of glycolic acid was 94 mol percent.

EXAMPLE 6

This was a repeat of Example 5, except that the 59.8 g of HF was replaced by 59.5 g of sulfuric acid. After 60 minutes of reaction, formaldehyde conversion was only 30%. After 360 minutes, formaldehyde conversion as 70%.

EXAMPLE 7

The reactor of Example 1 was charged with 0.5 mol of formaldehyde, 1.0 mol of water, 1.0 mol of glycolic acid and 0.015 mol of sulfuric acid. The reactor was pressured to 1000 psig with carbon monoxide at 50° C. There was no carbon monoxide uptake during 120 minutes reaction time. No conversion of formaldehyde could be measured.

EXAMPLE 8

The reactor of Example 1 was charged with 1.0 mol of formaldehyde, 0.5 mol of water, and 2.5 mols of hydrogen fluoride. The reactor was pressured with carbon monoxide to 2000 psig at 50° C. After 60 minutes of reaction time, formaldehyde conversion was greater than 99 mol percent. The yield of glycolic acid was 91 mol percent and of diglycolic acid, 5 mol percent.

EXAMPLE 9

The reactor was charged with 30 g (1.0 mol) of formaldehyde and 50 ml of HF. It was then sealed and charged with 1940 psig of carbon monoxide at 23° C. After 30 minutes, the reaction mixture was analyzed. Formaldehyde conversion was 95%. The yields of glycolic acid and diglycolic acid were 34% and 45%, respectively.

EXAMPLE 10

Example 9 was repeated using 50 g (1.7 mols) of formaldehyde. After 80 minutes, there was a 93% conversion of formaldehyde, and a 23% and 52% yield of glycolic acid and diglycolic acid, respectively.

EXAMPLE 11

A stainless-steel reactor having a capacity of 213 ml was charged with 20 g (1 mol) of hydrogen fluoride, 6 g (0.2 mol) of formaldehyde, and 3.6 g (0.2 mol) of water. The reactor was then charged with carbon monoxide to a pressure of 50 psig at 21° C. After 2 hours of agitation at these conditions, the reactor was opened and the contents were analyzed as in the previous examples. The reaction product contained 44 mol percent formaldehyde and 52.2 mol percent glycolic acid, representing a 93% yield of glycolic acid at a 56% conversion of formaldehyde.

EXAMPLE 12

Example 11 was repeated except that 3.6 g (0.04 mol) of $HBF_4$ was also added and the reaction time was only 1 hour. In this case, the reaction product contained 23 mol percent formaldehyde and 76 mol percent glycolic acid, which represents a 98% yield of glycolic acid based on a 77% conversion of formaldehyde. Example 1 illustrates the process of the present invention carried in a batch operation at low temperature. Even at a temperature in the range of −1° to 22° C, the yield of glycolic acid was 95% after 10 minutes of reaction time.

Example 2 was carried out in a manner similar to Example 1, but at one-half the initial pressure. Reaction times, conversion of reactants and yields were essentially the same.

Example 3 was again similar to Example 1, except the initial pressure was only 500 psig. Good yields and conversions were obtained after 24 minutes of reaction time.

Example 4 illustrates the effect of reducing the quantity of HF. High yields and conversions are obtained in 30 minutes.

Example 5 illustrates a run at higher temperatures, about 50° C, moderate pressures and even higher reactant-to-HF ratio. Again conversion is quantitative and yields of glycolic acid are high after 60 minutes of reaction time.

Example 6 is a run carried out under essentially the same conditions as Example 5, except that the HF was replaced by an equal weight of sulfuric acid. In this case, the conversion of reactants was only 30% in 60 minutes. A comparison of Examples 5 and 6 shows that HF is a surprisingly better catalyst for this reaction. With HF the rate is such that the reaction is complete in 60 minutes, but with sulfuric acid the rate is so slow that the reaction is only 70% complete in 6 hours.

Example 7 follows the preferred mode of operation described in U.S. Pat. No. 2,153,064, except at a temperature of 50° C. There was no reaction after 2 hours. In order to effect reaction in a reasonable time using a catalytic amount of sulfuric acid along with a large amount of glycolic acid, it is necessary to operate at temperatures above 150° C.

Example 8 was carried out utilizing a higher ratio of formaldehyde to water, thereby producing 5% diglycolic acid and 91% of glycolic acid in 60 minutes. Even better yields of diglycolic acid can be obtained using higher formaldehyde:water ratios. Example 8 illustrates a method for carrying out the process of this invention whereby essentially one part of glycolic acid is made per each 1.5 parts of reaction mixture. Using sulfuric acid, as in the preferred embodiment of U.S. Pat. No. 2,153,064 produces one part of glycolic acid per each 3.3 parts of reaction mixture (calculated on the basis of 100% yield from a reaction mixture having the same composition as Example 7.

Examples 9 and 10 illustrate that the reaction can be carried out in an anhydrous system to obtain a mixture of both glycolic and diglycolic acid. By carrying out this reaction in the presence of increasing amounts of water, the ratio of glycolic acid:diglycolic acid is increased, until glycolic acid becomes essentially the only product.

A comparison of Examples 11 and 12 shows about a 3-fold rate increase due to the catalytic influences of $HBF_4$.

I claim:

1. A process for producing hydroxyacetic acid which comprises contacting carbon monoxide with formaldehyde and a catalyst comprising hydrogen fluoride in a reaction zone and under reaction conditions effective to form hydroxyacetic acid, including a temperature between 0° and 100° C. and a carbon monoxide partial pressure between 10 and 4000 psig.

2. A process in accordance with claim 1 wherein the carbon monoxide is also contacted with water in the reaction zone.

3. A process in accordance with claim 1 wherein the temperature is between 20° and 60° C. and the carbon monoxide partial pressure between 10 and 3,000 psig.

4. A process in accordance with claim 2 wherein the formaldehyde and water are fed to the reaction zone at a mol percent of 3 to 35 formaldehyde; 3 to 35 water; and 40 to 90 HF; and the carbon monoxide partial pressure is maintained at 10 to 3000 psig in the reaction zone.

5. A process for producing hydroxyacetic acid and oxydiacetic acid which comprises contacting carbon monoxide with formaldehyde and a catalyst comprising hydrogen fluoride in a reaction zone and under reaction conditions effective to form hydroxyacetic acid, including a temperature between 0° and 100° C. and a carbon monoxide partial pressure between 10 and 4000 psig.

6. A process for producing oxydiacetic acid which comprises contacting carbon monoxide with formaldehyde and a catalyst comprising hydrogen fluoride and under reaction conditions effective to form oxydiacetic acid, including substantially anhydrous reaction conditions and a temperature between 0° and 100° C. and a carbon monoxide partial pressure between 10 and 4000 psig.

7. A process for producing hydroxyacetic acid which comprises contacting carbon monoxide with formaldehyde and a catalyst comprising HF and $HBF_4$ in a reaction zone and under conditions effective to form hydroxyacetic acid, including a temperature between 0° and 100° C and a carbon monoxide partial pressure between 10 and 4000 psig.

* * * * *